Figure 1:
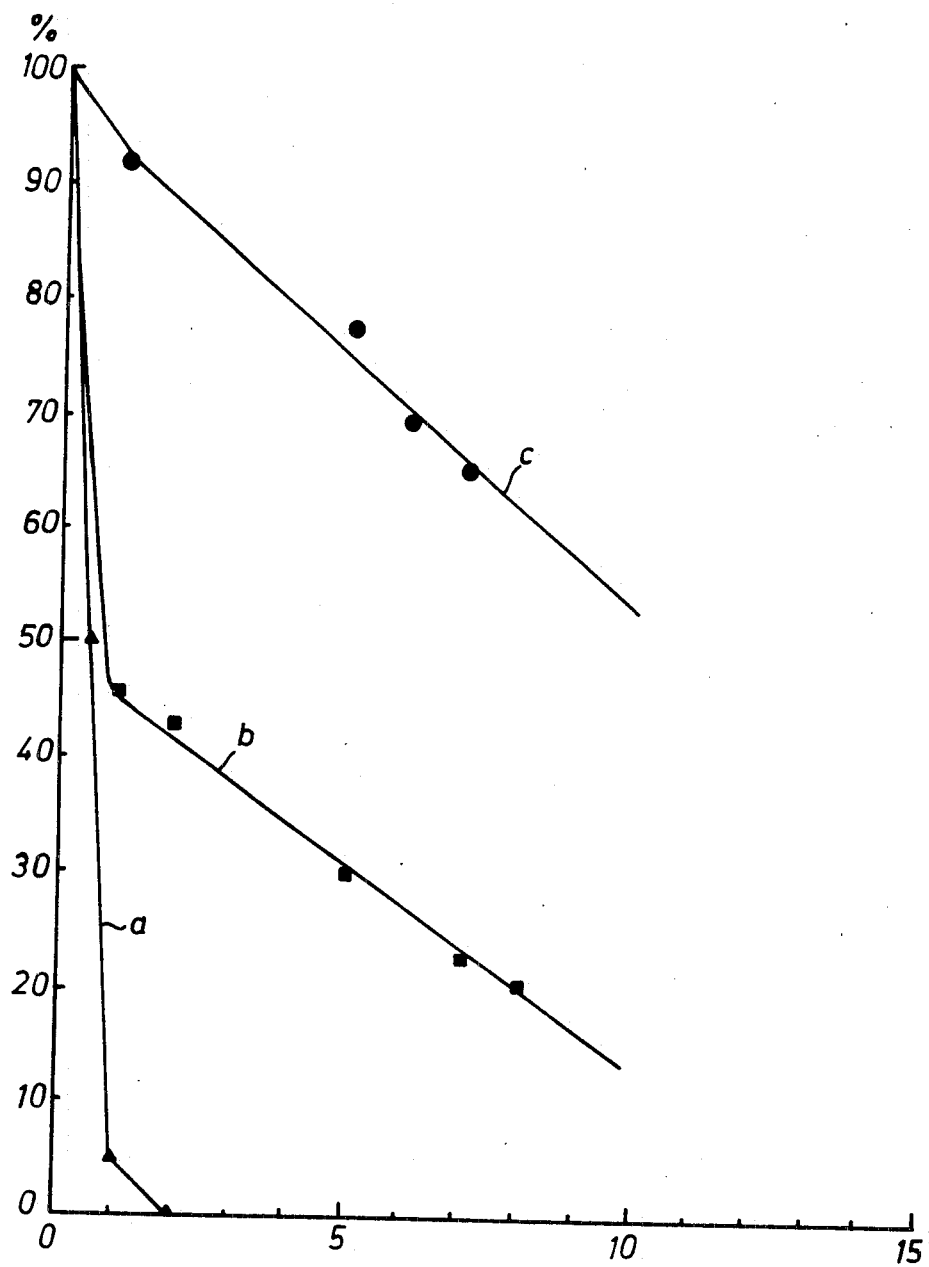

United States Patent [19]

Hüper

[11] 4,167,446

[45] Sep. 11, 1979

[54] WATER SOLUBLE CARRIER-BOUND PENICILLINACYLASE

[75] Inventor: Fritz Hüper, Wuppertal, Fed. Rep. of Germany

[73] Assignee: Bayer Aktiengesellschaft, Fed. Rep. of Germany

[21] Appl. No.: 627,132

[22] Filed: Oct. 30, 1975

Related U.S. Application Data

[63] Continuation-in-part of Ser. No. 449,272, Mar. 8, 1974, abandoned.

[30] Foreign Application Priority Data

Mar. 15, 1973 [DE] Fed. Rep. of Germany ....... 2312824

[51] Int. Cl.$^2$ .......................... C12D 9/00; C12D 9/06; C07G 7/02

[52] U.S. Cl. ...................................... 435/45; 435/178; 435/179

[58] Field of Search .................. 195/63, 68, DIG. 11, 195/36 P

[56] References Cited

U.S. PATENT DOCUMENTS

| | | | |
|---|---|---|---|
| 3,639,213 | 2/1972 | Ginger et al. | 195/63 |
| 3,649,457 | 3/1972 | Westman | 195/68 |
| 3,715,277 | 2/1973 | Dinella et al. | 195/63 |
| 3,736,230 | 5/1973 | Delin et al. | 195/36 P |
| 3,791,927 | 2/1974 | Forgione et al. | 195/63 |

*Primary Examiner*—David M. Naff
*Attorney, Agent, or Firm*—Jacobs & Jacobs

[57] ABSTRACT

A water-soluble non-colloidal penicillinacylase preparation containing penicillinacylase covalently bound to a water-soluble carrier is produced by reacting penicillinacylase with an activated derivative of a water soluble polysaccharide in aqueous solution. The water-soluble penicillinacylase preparation efficiently hydrolyzes penicillin and permits recovery of 6-aminopenicillanic acid efficiently in extremely high purity.

22 Claims, 3 Drawing Figures

WATER SOLUBLE CARRIER-BOUND PENICILLINACYLASE

CROSS-REFERENCE

This is a continuation-in-part of Ser. No. 449,272 filed Mar. 8, 1974, now abandoned.

The present invention relates to enzymatic compositions containing penicillinacylase (E.C. 3.5.1.11), to a process for their production, and to the use of such compositions in the production of 6-aminopenicillanic acid.

Penicillinacylase is an enzyme used in large-scale industrial processes for the production of 6-aminopenicillanic acid (6-APA), an intermediate which is valuable for the preparation of a wide variety of semi-synthetic penicillins.

According to German patent specification No. 1,111,778, a solution of benzylpenicillin is treated with a bacterial slurry containing penicillanacylase. As a result of the catalytic action of the enzyme, the side chain carbamide grouping of the penicillin is hydrolytically cleaved yielding 6-APA without opening of the $\beta$-lactam ring. This process has a significant disadvantage in that the 6-APA obtained contains many impurities which originate, inter alia, from the nutrient medium, the fermentation liquor and the bacteria. In addition, the enzymatic activity of the bacterial suspension is virtually spent after a single use, so that it cannot be re-used.

To avoid these disadvantages, water-insoluble enzymatic preparations containing penicillinacylases have been used instead of a bacteria suspension.

Various methods by which such compositions can be prepared have already been disclosed:

1. Covalent bonding of the enzyme to a water-insoluble carrier (G. J. H. Melrose, Rev. Pure and Appl. Chem. 21, 83 (1971) and U.S. Pat. No. 3,736,230.)
2. Inclusion of the enzyme in the lattice of a porous gel (K. Mosbach, R. Mosbach, Acta Chem. Scand. 1966, 20, 2807).
3. Micro-encapsulation [T. M. S. Chang, Nature 229, 117 (1971)].
4. Inclusion of the enzyme in the fibrous structure (German Published Specification No. 1,932,426).

All of the above are water-insoluble enzymic preparations which are heterogeneous compositions. They have the distinct advantage of being separated by simple filtration for reuse after each reaction. On the other hand, however, they suffer from several disadvantages and in fact, to date it has been impossible to transfer the processes described in German Published Specifications Nos. 1,917,057 and 1,907,365 for the preparation of 6-APA with penicillinacylase covalently bound to a water-insoluble carrier to an industrial scale. The reasons for this are several. Firstly, the carrier is excessively susceptible to abrasion and mechanically is unsuitable for repeated use. Secondly, process yields are only moderate since low specific activities of carrier-bound penicillinacylases are achieved.

The insoluble enzymatic preparation described in German Published Specification Nos. 2,143,062 which employs penicillinacylase bound to solid, water-insoluble, adsorbing substances such as nylon through a water-soluble dialdehyde also had disadvantages in industrial use. In addition to a crosslinking of the enzyme molecules with one another, covalent crosslinking with the carrier can also occur when the latter contains active groups which are able to react with the dialdehyde. Insolublized penicillinacylase produced in this way can split off soluble protein as a result of hydrolysis. There are therefore limitations on the re-use of the insoluble composition produced in this way.

In processes in which enzymes are entrapped in porous polymers, conditions are required under which enzymes are easily denatured. Accordingly, high losses in yield must be accepted in the preparation of such insoluble compositions. In addition, enzymes can diffuse through the pores of the polymer into the reaction medium, resulting in a continuous deterioration of enzymatic activity.

In the process described in German Published Specification No. 1,932,426, enzymes are incorporated into an easily produced fibrous structure. The enzyme is included in separate cavities which prevent loss of the enzyme through diffusion. However, after incorporation of the enzyme in the fiber, a high proportion of the originally present enzyme activity is lost. Furthermore, while on the one hand the pore sizes of the fibers must be suficiently small that no enzyme can diffuse out, such small pore sizes also restrict the diffusion of the substrate through the fiber structure to the enzyme and the subsequent rediffusion of the reaction products to the reaction medium. The incorporated enzyme is accordingly not utilized to its optimum extent. The incorporated enzyme is also in an unbound form and free enzymes are denatured more rapidly than enzymes covalently bound to carriers [H. D. Orth and W. Brümmer, Angewandte Chemie, 84, pages 319–368 (1972)]. For these various reasons, enzymes incorporated in polymers are accordingly inferiour to enzymes covalently bound to water-insoluble carriers.

It is known that enzymes can be bound to water-soluble carriers. Thus, according to U.S. Pat. No. 3,625,827, enzymes are coupled to a water-soluble ethylene-maleic anhydride copolymer. However, this process is not suitable for the preparation of high molecular enzyme derivatives since the carrier used becomes insoluble as the molecular weight increases. Furthermore, the enzyme can also react at several sites and with different polymer molecules, resulting in crosslinking which results in the enzyme-polymer derivative becoming insoluble.

Water-soluble enzymatic compositions such as streptokinase are disclosed in U.S. Pat. No. 3,639,213. These products, which are intended for medicinal use, are however colloidal. In the commercial preparation of 6-APA from natural penicillins through enzymatic means, it is necessary to remove impurities such as bacterial protein, which are capable of causing allergenic reactions. Such impurities are also generally colloidal in nature and are thus removed by filtration utilizing filters the pore diameters of which are smaller than the colloidal protein dimensions. Colloidal enzymatic preparations such as the streptokinase product described in U.S. Pat. No. 3,639,213 also would be removed by such filtration steps along with the undesired colloidal protein impurities and would thus be limited to a single use since the material would be contaminated with the colloidal protein impurities.

The present invention pertains to a water-soluble enzymatic composition comprising penicillinacylase covalently bound to a water-soluble polysaccharide carrier. The water-soluble compositions of the present invention are useful as above noted in the production of 6-APA from penicillins by the enzymic splitting of the 6-position side chain of the pencillin leaving the 6-APA nucleus for isolation and recovery.

The preferred water-soluble polysaccharide carriers are dextran, starch, levan and carboxymethylcellulose. The water-soluble composition is produced by reacting an activated derivative of the polysaccharide in aqueous solution with the pencillin-acylase. Preferably, the polysaccharide is reacted with a cyanogen halide to produce the activated derivative. Cyanogen chloride, cyanogen bromide and cyanogen iodide are all useful but cyanogen bromide is preferred. The water-soluble enzymatic composition can be obtained in almost quantitative yield, as appears from the enzymatic activities of the starting materials and the resulting products.

The water-soluble enzymatic composition of the present invention can be used as such or incorporated or encapsulated in a water-insoluble polymer which may be a polymeric matrix in which the water-soluble enzyme composition is dispersed, or a fibrous polymer in the interstices of which the water-soluble composition is trapped. A preferred polymeric matrix is a copolymer of acrylamide and N,N'-methylene-bis-acrylamide but others, such as ethylene-maleic anhydride polymers, may also be used. Such an embodiment can be produced by polymerizing the water-insoluble polymer in the presence of the water-soluble enzyme preparation of the invention. Alternatively, a fibrous polymeric carrier can be spun in the presence of the water-soluble composition.

The present invention also includes an improved process for the production of 6-APA which comprises contacting the water-soluble enzymatic composition of the present invention with a penicillin. The water-soluble enzymatic composition is used in aqueous solution and can be recovered from the reaction from the aqueous reaction mixture by ultrafiltration for repeated re-use. As compared to the unbound enzyme, the enzymatic composition according to the present invention has the great advantage of being more stable, even at higher penicillin concentrations.

Moreover, since aqueous solutions of this enzymatic composition are not colloidal, reaction solutions of any starting penicillin, the water-soluble enzymatic preparation, the products of the conversion, and various impurities including colloidal protein can be filtered through a suitable filter, e.g. one having an average pore diameter of 0.8–1.0μ, to yield a filtrate which contains both 6-APA and the enzyme preparation but no colloidal material such as protein. The penicillinacylase polysaccharide product is thus non-colloidal in nature and is separated from the 6-APA through the utilization of ultrafiltration; i.e., filtration which permits the passage of material having a molecular weight less than 100,000. The penicillinacylase polysaccharide product thus recovered can be reused with little or no loss of enzymatic activity. In contrast to a colloidal preparation, it is free of colloidal protein impurities. This is particularly important in the preparation of penicillins having low allergenicity.

If a polysaccharide is first reacted with a cyanogen halide to produce an activated derivative and this is then reacted with penicillinacylase to produce the water-soluble composition of the invention, the course of the reaction can be represented by the following equation:

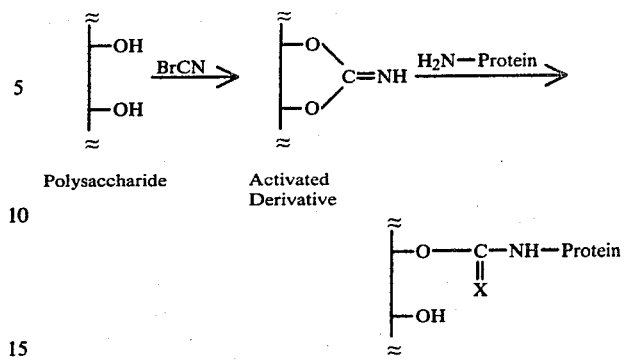

wherein X is NH or an oxygen atom and "H₂N-Protein" is the penicillinase.

Water is generally used as the diluent or solvent and reaction temperatures are generally between 0° C. and 50° C. The reaction can be carried out both under normal pressure and under elevated pressure. During the preparation of the activated derivative, the reaction medium is generally kept in the pH range of 8 to 13, preferably at pH 11.0, by adding a base, fc. example, sodium hydroxide solution. The reaction of the cyanogen halide with the polysaccharide is usually complete after 10 to 20 minutes. No cyanogen halide should remain in the solution when the activated derivative is reacted with penicillinacylase in the next step. Also, the next step must be carried out as soon as possible since the activated derivative can easily be inactivated by hydrolysis. Before the reaction with penicillinacylase, the pH value of the solution containing the activated derivative is preferably adjusted to 8.5. After addition of the penicillinacylase, the mixture is stirred at 0° C.–50° C., preferably 5° C.–10° C. The content of unreacted enzyme can be determined if dextrans of molecular weight of about 500,000 are used. For example, the high molecular water-soluble composition can be separated from the unbound enzyme by ultrafiltration using membrances impermeable to molecules of molecular weight exceeding 100,000.

The ratio of polysacchride, cyanogen halide and penicillinacylase can be varied within wide limitations. Complete conversion of the enzyme is reliably achieved if at least 5 parts by weight of polysaccharide are used per part by weight of enzymatic protein.

Figure 2:
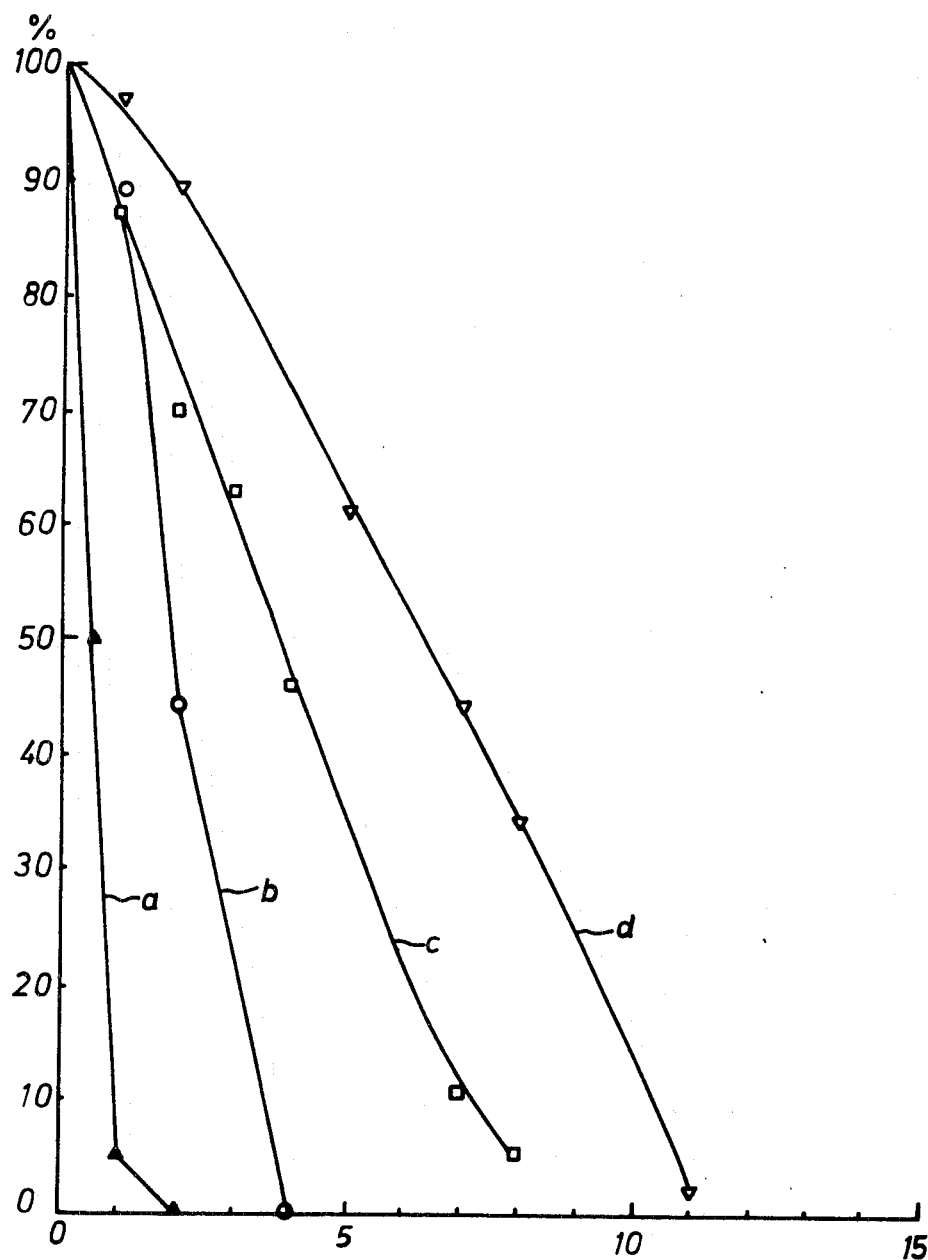

The ratio of the amounts of cyanogen halide and polysaccharide has an extraordinary influence on the stability of the water-soluble composition. Natural penicillinacylase in aqueous solution of pH 7.8 at 45° C. is inactivated to the extent of up to 95% within 24 hours (see FIG. 1, curve a). Under identical conditions, the water-soluble composition of the invention containing, as polymeric carrier, dextran of molecular weight 500,000, only loses 47% of its activity in 24 hours, if 17 mg of cyanogen bromide are employed per gram of dextran (see FIG. 1, curve b). However, if 80 mg of cyanogen bromide are used per gram of dextran, the enzymatic activity only decreases by 5% in 24 hours (see FIG. 1, curve c). It is surprising that, at constant coupling yield, the stability of the water-soluble composition can be increased extra-ordinarily by increasing the proportion of cyanogen halide. Possibly, more covalent bonds are formed between the carrier molecule and the enzyme molecule as a result of increasing the amount of cyanogen halide which could lead to the tertiary structure of the enzyme being increasingly stabilized as the number of covalent bonds increases. The amount of cyanogen halide employed is, however, limited because sparingly soluble and/or insoluble enzyme derivatives can be produced as a result of crosslinking. Thus, it is not advisable to employ more than about 150 mg of cyanogen bromide per gram of polysaccharide of molecular weight of about 500,000. If a lower molecular weight polysaccharide is employed, for example dextran of a molecular weight of 20,000, there is no problem in using 300 mg of cyanogen bromide per gram of polysaccharide. However, the use of polysaccharides of lower molecular weights reduces the stability of the enzyme. FIG. 2 shows the variation with time of the residual activities of water-soluble penicillin-acylase-dextran compositions according to the invention after preincubation at 45° C. and pH 7.8. In this Figure, the curves represent the following:

Curve a: unbound penicillinacylase.
Curve b: penicillinacylase covalently bound to dextran of approximate molecular weight 20,000 (80 mg of cyanogen bromide per gram of dextran).
Curve c: as in b, but 160 mg of cyanogen bromide per gram of dextran.
Curve d: penicillinacylase covalently bound to dextran of approximate molecular weight 60,000 (80 mg of cyanogen bromide per gram of dextran).

Eighty milligrams of cyanogen bromide were used per gram of dextran to obtain curves (b) and (d). It was possible to improve perceptibly the stability of the composition by using twice as much cyanogen bromide as in experiment (d)—see curve (c).

Figure 3:
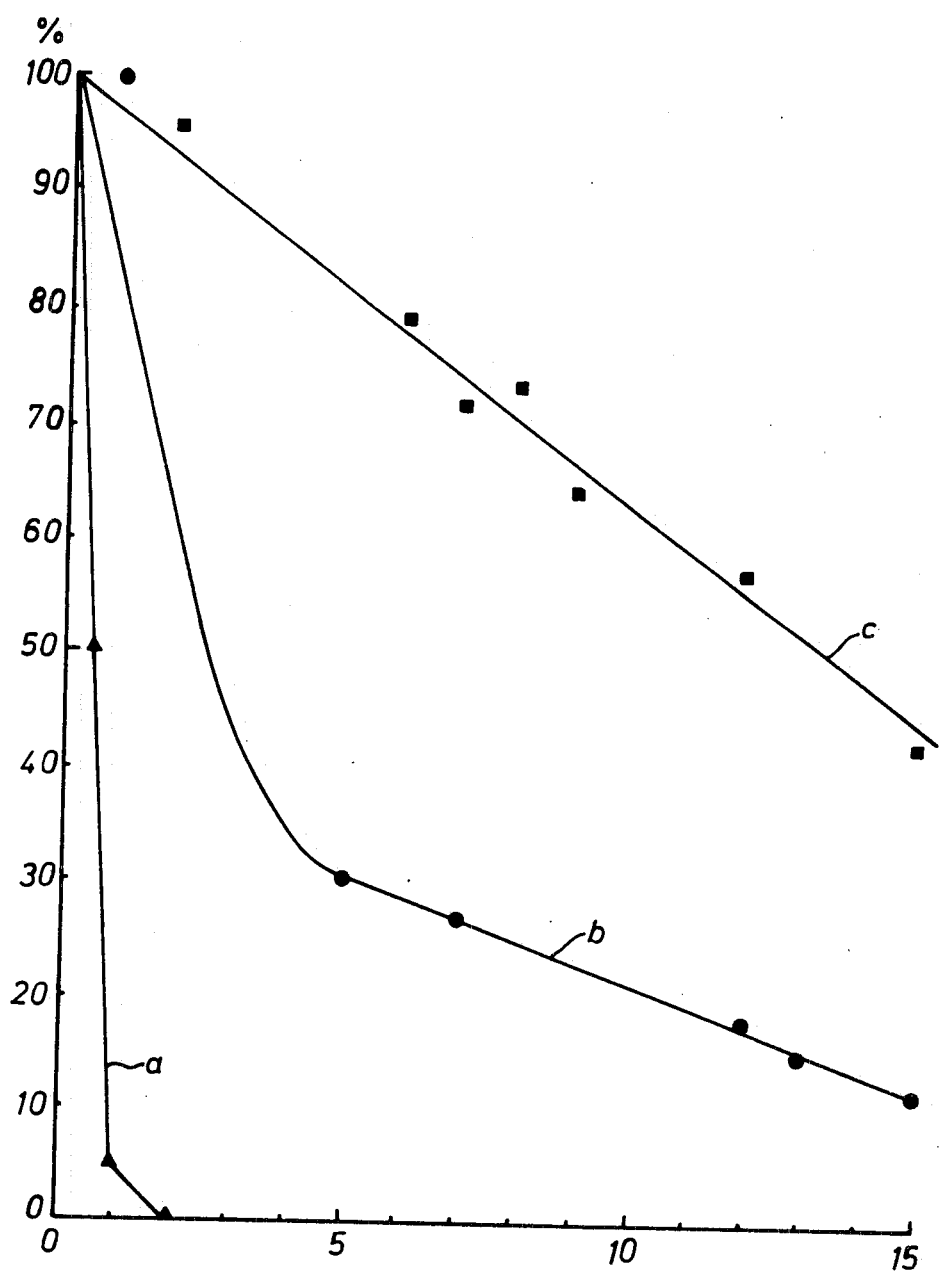

With starch as the water-soluble carrier, extremely stable water-soluble compositions according to the invention can be produced. The stability of the composition again depends on the amount of cyanogen halide employed. Preferably, at least 150 mg of cyanogen bromide are used for the reaction per gram of starch. The distinct stabilization of the penicillinacylase by covalent bonding to starch, in accordance with the invention, is illustrated by FIG. 3. The curves show the residual activities after pre-incubation at 45° C. and pH 7.8, as follows:

Curve a: unbound penicillinacylase.
Curve b: penicillinacylase bound to starch (80 mg of cyanogen bromide per gram of starch).
Curve c: penicillinacylase bound to starch (160 mg of cyanogen bromide per gram of starch).

As stated above, the water-soluble compositions prepared in this way can, according to the invention, be encapsulated or incorporated in water-insoluble polymers, thereby rendering the enzyme preparation water-insoluble. It is particularly advantageous to encapsulate them in fibers by spinning or to incorporate them in a polymerization mixture. Thus, for example, it is possible to incorporate, by polymerization, a penicillinacylase-dextran water-soluble composition according to the invention (dextran of molecular weight 500,000) in yields of 60% of the original enzymatic activity, using methods known from the literature (H. Nilsson, R. Mosbach and K. Mosbach, Biochim. Biophys. Acta 268 (1972) 253–256). In a control experiment with natural unbound penicillinacylase, only 10% of the originally present enzyme activity was obtained after incorporation by polymerization, under identical experimental conditions. The water-insoluble composition proved to be enzymically extremely stable even after being employed repeatedly for the preparation of 6-APA. The water-insoluble composition can be separated rapidly and simply from the reaction medium, for example by filtration, since the polymer can be produced in particle sizes of more than 1 mm in diameter. Moreover, increased resistance to mechanical abrasion can be incorporated in the polymer.

The new water-soluble composition displays strong enzymatic activity in the preparation of 6-APA from penicillin. Usually the enzymatic splitting of penicillins to produce 6-APA is carried out in dilute solutions in order not to inactivate the enzyme and prior to isolating the 6-APA, about 80% of the water must thus be removed by evaporation in order to achieve good yields of 6-APA. Since the compositions according to the invention allow the enzymatic hydrolysis to be carried out at high concentrations, less water has to be evaporated. Hence, the production of 6-APA using the penicillinacylase compositions of the invention is more economical than corresponding processes using unbound penicillins.

Examples of penicillins that may according to the invention be used in conjunction with the compositions of the invention to produce 6-APA are benzylpenicillin (Pen. G), phenoxymethylpenicillin (Pen. V) and salts such as potassium penicillin G. The reaction is generally carried out in aqueous solution with the continuous or repeated addition of a base such as triethylamine to neutralize the acid formed in the reaction. It is preferred to keep the pH between 7 and 8, especially at about 7.8. After the reaction is completed, the solution contains unconverted penicillin, phenylactic acid, and 6-APA. The reaction solution may also contain colloidal protein material which can be removed through use of an appropriate filter having a pore diameter of 0.8 to 1.0$\mu$, such as a Seitz EKS II filter. The enzyme preparation can be separated from the 6-APA by ultrafiltration. Commercially available membrane filters which are impermeable to molecules of molecular weights about 100,000 are particularly suitable for this purpose. The 6-APA formed is isolated according to known methods after removal of the composition, and can be crystallized, preferably at pH 4.3.

In the enzymatic hydrolysis of penicillin with the composition of the invention, substantially higher yields of 6-APA are obtained than when *E. coli* slurry is used. 6-APA has been isolated in yields of about 85–90%, according to the invention. The penicillinacylase compositions according to the present invention can be employed repeatedly over a long period. Even after long periods, enzymatic acitivity is almost completely retained. From the economic point of view, this stability after repeated reuse is of great importance.

The enzyme activities (U) quoted in the examples which follow are defined as the activity which hydrolyzes 1$\mu$ mol of penicillin G to 6-APA and phenylacetic acid, per minute at 37° C. and pH 7.8. The penicillinacylase used was prepared according to DOS 2 151 236.

The following non-limitative examples more particularly illustrate the present invention.

EXAMPLE 1

(a) 5 g of dextran 500, of approximate molecular weight 500,000, are dissolved in 165 ml of water and the solution is adjusted to pH 11.0 with 2 N sodium hydroxide solution. 85 mg of cyanogen bromide are added at a temperature of 20° C. while stirring and the pH value of the solution is kept at 11.0 with 2 N NaOH. 10 Minutes after addition of the cyanogen bromide, the solution is adjusted to pH 8.5 with 2 N hydrochloric acid and mixed with 170 ml of an aqueous solution of 550 mg of penicillinacylase (enzymatic activity 7.3 U/mg). The solution is stirred for 16 hours in a refrigerator at 4° C. After ultrafiltration, no enzyme activity is detectable in the filtrate. It may therefore be assumed that coupling with the carrier has taken place completely. The yield of enzymatic activity is 98% relative to the initial activity. After freeze-drying, the enzymic activity remains preserved completely.

A solution of the water-soluble composition thus produced was stored at 45° C. and pH 7.8 to test its stability. The residual activity determined after various times are shown in FIG. 1, curve b. Curve a was obtained correspondingly with natural, unbound penicillinacylase.

(b) 5 g of dextran 500, of approximate molecular weight 500,000, are dissolved in 165 ml of water and adjusted to pH 11.0 with 2 N sodium hydroxide solution. 400 mg of cyanogen bromide are added at a temperature of 20° C., while stirring, and the pH value of the solution is kept at 11.0 by means of 2 N sodium hydroxide solution. 20 Minutes after addition of the cyanogen bromide, the solution is adjusted to pH 8.5 with 2 N hydrochloric acid and mixed with 170 ml of an aqueous solution of 550 mg of penicillinacylase (enzymatic activity 7.3 U/mg). The solution is stirred for 16 hours in a refrigerator at 4° C. Under these conditions, the enzyme is bound completely to the carrier. The yield of enzymatic activity is 96% relative to the initial activity. The keeping quality of the water-soluble composition thus produced—determined as in Example 1(a)—is shown graphically in FIG. 1, curve c.

EXAMPLE 2

(a) 5 g of dextran 20 of approximate molecular weight 20,000 are reacted, as indicated in Example 1 (b), with 400 mg of cyanogen bromide and then with 550 mg of penicillinacylase. After the reaction, the yield of enzymatic activity is 96%, relative to the initial activity. The keeping quality of this water-soluble composition—determined as in Example 1 (a)—is shown graphically in FIG. 2, curve b.

(b) 5 g of dextran 20 are reacted, as indicated in Example 1 (b), with 800 mg of cyanogen bromide and then with 550 mg of penicillinacylase. The yield of enzymatic activity after the reaction is 87%, relative to the initial activity. The keeping quality of this water-soluble composition—determined as in Example 1 (a)—is shown graphically in FIG. 2, curve c.

(c) 5 g of dextran 60 of approximate molecular weight 60,000 are reacted, as indicated in Example 1 (b), with 400 mg of cyanogen bromide and then with 550 mg of penicillinacylase. The yield of enzymatic activity after the reaction is 99%, relative to the initial activity. The keeping quality of this water-soluble composition—determined as in Example 1 (a)—is shown graphically in FIG. 2, curve d.

EXAMPLE 3

(a) 5 g of soluble starch, prepared according to Zulkowsky, are dissolved in 165 ml of water and the solution is adjusted to pH 11.0 with 2 N sodium hydroxide solution. 400 mg of cyanogen bromide are added at a temperature of 20° C., while stirring, and the pH value of the solution is kept at 11.0 by means of 2 N NaOH. 20 Minutes after addition of the cyanogen bromide, the solution is adjusted to pH 8.5 with 2 N hydrochloric acid and mixed with 170 ml of an aqueous solution of 550 mg of penicillinacylase (enzymatic activity 7.3 U/mg). The solution is stirred for 16 hours in a refrigerator at 4° C. After the reaction, the yield of enzyme activity is 98%, relative to the initial activity. The water-soluble composition thus produced, which contains penicillinacylase bound to starch by covalent bonds, can be freeze-dried without loss of activity. Yield 6.2 g, with an enzymatic activity of 0.65 U/mg. The stability of the water-soluble composition was tested, as indicated in Example 1 (a), in aqueous solution at 45° C. and pH 7.8 (see graphical representation, FIG. 3, curve b).

(b) 5 g of soluble starch prepared according to Zulkowsky are reacted, as indicated in Example 3 (a), with 800 mg of cyanogen bromide and then with 550 mg of penicillin-acylase. After the reaction, the yield of enzyme activity is 98%, relative to the initial activity. The stability of the water-soluble composition thus produced was tested in aqueous solution at 45° C. and pH 7.8 (see graphical representation, FIG. 3, curve c). Yield after freeze-drying, 6.1 g, of enzymatic activity 0.65 U/mg.

EXAMPLE 4

210 ml of a solution of water-soluble penicillin-acylase-dextran composition, prepared according to Example 1 (b) and having an activity of 9.6 U/ml, are added to a solution of 63 g of potassium penicillin G in 800 ml of water and the mixture is stirred at 38° C. The pH value of the reaction mixture is kept constant at 7.8 by continuous addition of triethylamine. After 6 hours, no further triethylamine is taken up. The solution is filtered through an ultrafilter down to a residual volume of 100 ml, 250 ml of water are added to the residual solution and the mixture is again filtered down to 100 ml. The filtrate, including the wash water, is concentrated to 150 ml in vacuo. The 6-APA is precipitated at the isoelectric point at pH 4.3, in the presence of 100 ml of methyl isobutyl ketone, by addition of 6 N hydrochloric acid. After one hour, the 6-APA is filtered and rinsed with 100 ml of water and 100 ml of acetone. It is dried in vacuo at 40° C.; melting point 208° C.; yield 31.9 g of 6-APA, representing 87.2% of theory.

The water-soluble composition separated off by ultrafiltration can be employed for further splitting batches. After repeating the splitting five times, no enzyme activity has been consumed, so that the reaction time does not have to be lengthened.

EXAMPLE 5

210 ml of a solution of the water-soluble penicillin-acylase-dextran composition, of activity 9.6 U/ml, prepared according to Example 1 (b), are added to 63 g of potassium penicillin G and 290 ml of water and the mixture is stirred constant at 38° C. The pH value of the reaction mixture is kept constant at 7.8 by continuous addition of triethylamine. After 12 hours, no further triethylamine is taken up. The reaction batch is worked up analogously to Example 4. The enzymic solution separated off by ultrafiltration contains 92% residual activity. Yield of 6-APA 30.8 g (84% of theory).

In a parallel experiment with an equal amount of natural unbound penicillinacylase, unreacted penicillin was still present after a splitting time of 12 hours in a reaction mixture which was treated analogously. The residual penicillinacylase activity still present was 67% of theory. The water-soluble catalyst of the invention thus shows, under the same conditions, a better degree of conversion, and better retention of its activity, than unbound penicillinacylase.

EXAMPLE 6

2.9 g of water-soluble penicillinacylase-starch composition, having an activity of 650 U/g and prepared according to Example 3 (b), are dissolved in 600 ml of 0.05 M triethylanolamine/hydrochloric acid buffer of pH 7.0. 85.5 g of acrylamide, 4.5 g of N,N'-methylene-bis-acrylamide and 2.5 g of ammonium peroxydisulphate dissolved in 5 ml of the above buffer and 5 ml of N,N,N',N'-tetramethylethylenediamine are added to the solution (giving solution A).

2,900 ml of toluene, 1,100 ml of chloroform, 5 ml of N,N,N',N'-tetramethylethylenediamine and 10 ml of emulsifier 1736 (Bayer AG) are introduced into a three-necked flask equipped with a stirrer, cooled to 4° C. and stirred at a speed of 250 revolutions/minutes. Solution A is added dropwise from a dropping funnel, under nitrogen as a protective gas, the mixture is stirred for 30 minutes and the polymer is filtered off. It is rinsed twice with 1 liter of toluene and 2 liters of 0.5 M sodium chloride solution. The polymer contains 63% of the original penicillinacylase activity, and is water-insoluble.

The water-insoluble polymer containing the enzyme composition is added to a solution of 31.5 g of potassium penicillin G in 500 ml of water and the mixture is stirred at 38° C. The pH value of the reaction mixture is kept constant at 7.8 by addition of triethylamine. After 6 hours, no further triethylamine is consumed. The water-insoluble polymer is filtered off and washed with a little water. The filtrate, including the wash water, is concentrated to 80 ml in vacuo. The 6-APA is precipitated at the iso-electric point at pH 4.3, in the presence of 80 ml of methyl isobutyl ketone, by adding 6 N hydrochloric acid. After one hour, the 6-APA is filtered off and rinsed with 75 ml of water and 75 ml of acetone. It is dried in vacuo at 40° C. Melting point 208° C., yield 16.7 g (91% of theory).

The water-insoluble polymer can be used, without perceptible loss of enzymic activity, for at least 20 successive batches.

What is claimed is:

1. A water-soluble non-colloidal penicillinacylase composition comprising penicillinacylase covalently bound to a cyanogen halide activated water soluble polysaccharide.

2. A water-soluble non-colloidal penicillinacylase composition comprising penicillinacylase covalently bound to a cyanogen halide activated polysaccharide selected from the group consisting of dextran, water-soluble starch, levan and carboxymethylcellulose, said composition passing through a filter having a pore diameter of 0.8 to 1.0μ but not through a membrane which is impermeable to molecules of molecular weights of 100,000 or greater.

3. A water-soluble penicillinacylase composition according to claim 2 wherein the polysaccharide is dextran.

4. A water-soluble penicillinacylase composition according to claim 3 wherein the dextran is of a molecular weight of about 500,000.

5. A water-soluble penicillinacylase composition according to claim 3 wherein the polysaccharide is water-soluble starch.

6. A water-soluble penicillinacylase composition according to claim 3 wherein the polysaccharide is levan.

7. A water-soluble penicillinacylase composition according to claim 3 wherein the polysaccharide is carboxymethylcellulose.

8. A water-soluble penicillinacylase composition according to claim 2 dispersed or entrapped in a water-insoluble carrier.

9. Process for the preparation of a water-soluble non-colloidal penicillinacylase composition according to claim 2 which comprises allowing penicillinacylase to react in an aqueous medium with the reaction product of said polysaccharide and a cyanogen halide.

10. The process according to claim 9 wherein said cyanogen halide is cyanogen bromide.

11. The process according to claim 9 wherein the pH of the solution during reaction is about 8.5.

12. The process according to claim 11 wherein the reaction temperature is from about 5° C. to about 10° C.

13. The process according to claim 9 wherein the reaction product of the polysaccharide and a cyanogen halide is that obtained from dextran and cyanogen bromide.

14. The process according to claim 13 wherein the dextran is of a molecular weight of about 500,000.

15. The process according to claim 14 wherein about 800 mg of cyanogen bromide are used per gram of dextran.

16. The process according to claim 9 wherein the reaction product of the polysaccharide and a cyanogen halide is that obtained from water-soluble starch and cyanogen bromide.

17. The process according to claim 9 wherein the reaction product of the polysaccharide and a cyanogen halide is that obtained from levan and cyanogen bromide.

18. The process according to claim 9 wherein the reaction product of the polysaccharide and a cyanogen halide is that obtained from carboxymethylcellulose and cyanogen bromide.

19. In the process for the production of 6-aminopenicillanic acid in which a penicillin is treated with an enzymatic material capable of hydrolytically removing the 6-position side chain, the improvement which comprises using as said enzymatic material a water-soluble non-colloidal penicillinacylase composition comprising penicillinacylase covalently bound to a water-soluble cyanogen halide activated polysaccharide.

20. The process according to claim 19 wherein said polysaccharide is dextran, water-soluble starch, levan or carboxymethylcellulose.

21. In the process for the production of 6-aminopenicillanic acid in which a penicillin is treated with an enzymatic material capable of hydrolytically removing the 6-position side chain, the improvement which comprises using as said enzymatic material a water-soluble non-colloidal penicillinacylase composition comprising penicillinacylase covalently bound to a cyanogen halide-activated polysaccharide selected from the group consisting of dextran, water-soluble starch, levan or carboxymethylcellulose, said composition passing through a filter having a pore diameter of 0.8 to 1.0μ but not through a membrane which is impermeable to molecules of molecular weights of 100,000 or greater.

22. The process according to claim 21 wherein the polysaccharide is dextran or water-soluble starch.

* * * * *